United States Patent [19]

Long

[11] Patent Number: 4,678,435

[45] Date of Patent: Jul. 7, 1987

[54] TEMPORARY DENTAL CROWN AND METHOD OF FORMING THE SAME

[76] Inventor: Harry A. Long, 75 Mountain Spring Dr., Sparta, N.J. 07871

[21] Appl. No.: 890,104

[22] Filed: Jul. 28, 1986

[51] Int. Cl.$^4$ .............................................. A61C 5/08
[52] U.S. Cl. .................................................... 433/218
[58] Field of Search ............................... 433/218, 219

[56] References Cited

U.S. PATENT DOCUMENTS

| | | | |
|---|---|---|---|
| 3,566,469 | 3/1971 | Pelizzari | 433/213 |
| 4,015,332 | 4/1977 | Manne | 433/219 |

Primary Examiner—Robert Peshock
Attorney, Agent, or Firm—Daniel H. Bobis

[57] ABSTRACT

A shell for producing a temporary dental prosthesis such as a temporary dental crown includes an occlusal layer having an outer surface shaped to provide a tooth-like appearance; a buccal side connected to one edge of the occlusal layer and extending down therefrom; a lingual side connected to an opposite edge of the occlusal layer and extending down therefrom; and the shell being open along mesial and distal sides thereof.

Additionally, forming a temporary dental prosthesis, by first grinding to make a prepared tooth; using a shaped shell filled with a self-curing acrylic resin material in an unhardened state; the shaped shell is positioned over the prepared tooth such that the buccal and lingual sides thereof cover buccal and lingual sides of the prepared tooth and the respective free edges of the buccal and lingual sides of the shell are proximate to the adjacent gingival surface about the prepared tooth; the acrylic resin is permitted to set such that the acrylic resin bonds to the shell to form the temporary dental crown; the formed temporary dental crown is then removed, shaped and polished and then cemented back onto the prepared tooth.

4 Claims, 16 Drawing Figures

TEMPORARY DENTAL CROWN AND METHOD OF FORMING THE SAME

BACKGROUND OF THE INVENTION

This invention relates generally to temporary dental prostheses and, more particularly, is directed to a temporary dental crown and a method of forming the same.

The formation of single unit temporary posterior crowns has posed a problem for dentists for many years. Generally, the methods presently being used are cumbersome, both in the actual steps that must be performed and the materials that must be used, requiring large amounts of time and high costs for preparing the crowns. In addition, conventional methods of forming temporary crowns suffer from various disadvantages, such as poor aesthetic appearance, poor marginal adaptation, imprecision in the interproximal contact areas, uncontrolled occlusal contact and physiologically inferior labial and lingual contours.

As an example, U.S. Pat. No. 2,930,124 discloses a dental crown and method of producing the same. In this Patent, a hollow cylindrical member made of metal has a plurality of projections on its inner surface adapted to secure the member to the prepared tooth. Because a cylindrical member is used, however, it is difficult to match the appearance of the crown to the adjacent teeth, whereby the aesthetic appearance is not as desirable as it should be. Further, the marginal adaptation and interproximal contact areas do not provide optimum results. The same holds true as to the labial and lingual contours and the occlusal contact.

U.S. Pat. No. 3,585,723 also discloses a dental crown and a method of installation thereof, which relies on the expansion of the cervix of the crown along the mesiodistal axis as the crown moves toward the cervical end. Because a continuous side wall is provided for the crown, the same disadvantages that accrue from U.S. Pat. No. 2,930,124 also apply to this Patent.

The same holds true with respect to U.S. Pat. Nos. 853,984 and 4,206,545, both of which disclose a crown with a continuous side wall, including mesial and distal sides, and which are affixed to the prepared tooth using a filler and cement, and the pressure of the patient's natural bite. U.S. Pat. No. 4,206,545 also teaches the use of a trimmed cervical border to adapt to the many gingival shapes present in nature.

Other patents which are less relevant than the above are U.S. Pat. Nos. 3,793,728; 3,949,476 and 4,504,230.

OBJECTS AND SUMMARY OF THE INVENTION

Accordingly, it is an object of the present invention to provide a temporary dental crown that has superior aesthetic appearance.

It is another object of the present invention to provide a temporary dental crown having superior marginal adaptation.

It is still another object of the present invention to provide a temporary dental crown having precise interproximal contact areas.

It is yet another object of the present invention to provide a temporary dental crown having controlled occlusal contact.

It is a further object of the present invention to provide a temporary dental crown having physiologically superior labial and lingual contours.

It is a still further object of the present invention to provide a temporary dental crown that is fitted more precisely to the patient's mouth than conventional dental crowns.

It is a yet further object of the present invention to provide a temporary dental crown formed from a shell having its mesial and distal sides open.

In accordance with an aspect of the present invention, a shell for producing a temporary dental prosthesis, includes an occlusal layer having an outer surface shaped to have a tooth-like appearance; a buccal side connected to one edge of the occlusal layer and extending down therefrom; a lingual side connected to an opposite edge of the occlusal layer and extending down therefrom; and the shell being open along mesial and distal sides thereof.

In accordance with another aspect of the present invention, a method of making a temporary dental prosthesis, includes the steps of grinding down a tooth to form a prepared tooth; filling a shell having an occlusal layer with an outer surface shaped to have a tooth-like appearance, buccal and lingual sides connected to opposite edges of the occlusal layer and extending down therefrom, and open mesial and distal sides, with a self-curing acrylic resin material in an unhardened state; positioning the shell over the prepared tooth such that the buccal and lingual sides thereof cover buccal and lingual sides of the prepared tooth and the respective free edges of the buccal and lingual sides of the shell are proximate to the adjacent gingival surface about the prepared tooth; permitting the acrylic resin to set such that the acrylic resin bonds to the shell to form the temporary prosthesis; and shaping and polishing the temporary prosthesis.

The above and other objects features and advantages of the present invention will become readily apparent from the following detailed description thereof which is to be read in connection with the accompanying drawings.

DETAILED DESCRIPTION OF A PREFERRED EMBODIMENT

Figure 1:
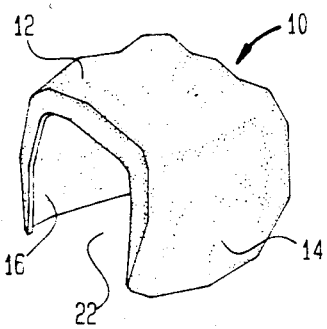
FIG. 1 is a front perspective view of a shell for forming a temporary dental crown according to the present invention.
Figure 2:
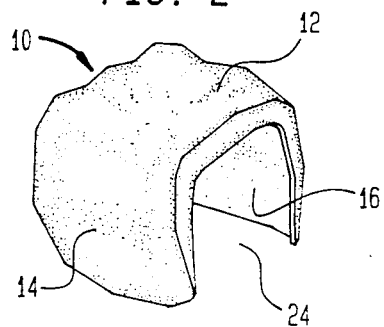
FIG. 2 is a perspective view of the shell of FIG. 1.
Figure 3:
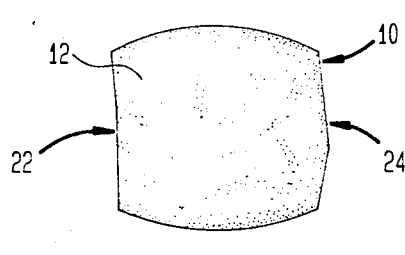
FIG. 3 is a top plan view of the shell of FIG. 1.
Figure 4:
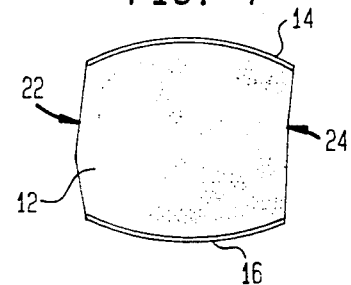
FIG. 4 is a bottom plan view of the shell of FIG. 1.
Figure 5:
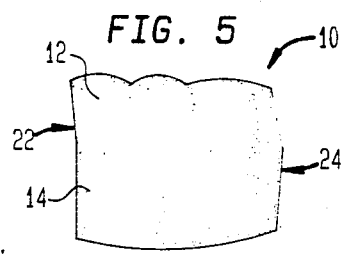
FIG. 5 is a buccal side plan view of the shell of FIG. 1.
Figure 6:
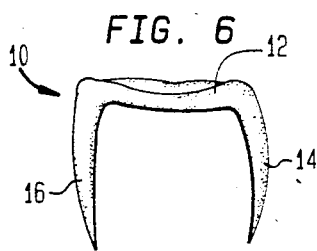
FIG. 6 is a mesial end plan view of the shell of FIG. 1.

Referring to the drawings in detail, and initially to FIGS. 1-6 thereof, a prefabricated plastic shell 10 for use in producing a temporary dental crown according to the present invention includes an occlusal layer 12 having an outer surface shaped to have a tooth-like appearance. Preferably, occlusal layer 12 has a substantially square or rectangular configuration with a defined thickness. A buccal side 14 is connected to one edge of occlusal layer 12 and extends down therefrom. In like manner, a lingual side 16 is connected to an opposite edge of occlusal layer 12 and extends down therefrom. Buccal and lingual sides 14 and 16 preferably taper in thickness from occlusal layer 12 to the opposite free edges 18 and 20, respectively, thereof. In addition, buccal and linqual sides 14 and 16, as shown in FIG. 6, preferably have a slightly convex configuration to better approximate the actual shape of a tooth, and thereby the outer surfaces thereof have a tooth-like appearance. The widths of buccal and lingual sides 14 and 16 will vary to assure a snug sub-gingival fit.

It is an important aspect of the present invention that the mesial side 22 and distal side 24 of shell 10 be open in order to provide superior marginal adaptation and precise interproximal contact areas with adjacent teeth, in addition to a superior aesthetic appearance, as will be apparent from the description which follows.

Figure 7:
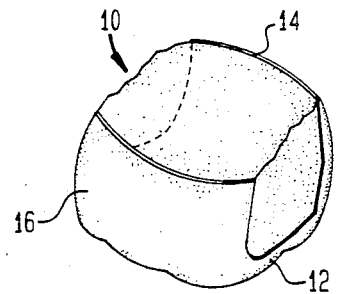
FIG. 7 is a bottom perspective view of the shell of FIG. 1 filled with an acrylic resin material.
Figure 8:
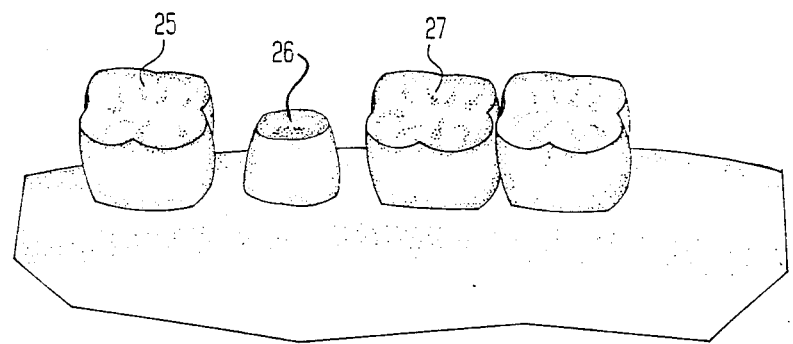
FIG. 8 is a perspective view of several teeth, one of which has been prepared to receive a temporary dental crown formed with the shell of FIG. 1.
Figure 9:
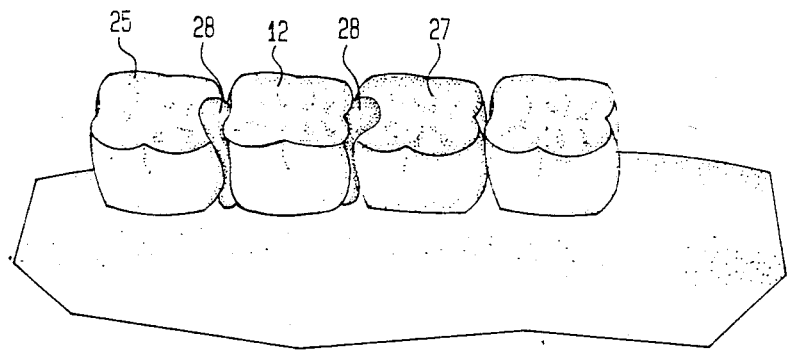
FIG. 9 is a perspective view of the shell of FIG. 7 filled with acrylic resin positioned on the ground down tooth of FIG. 8, shown with acrylic resin oozing out of the shell in its unfinished state.
Figure 10:
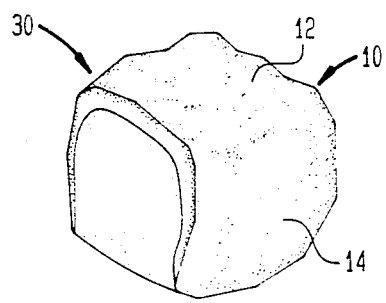
FIG. 10 is a front perspective view of the finished and polished temporary crown formed with the shell of FIG. 1, prior to cementing the same to the ground down tooth.
Figure 11:
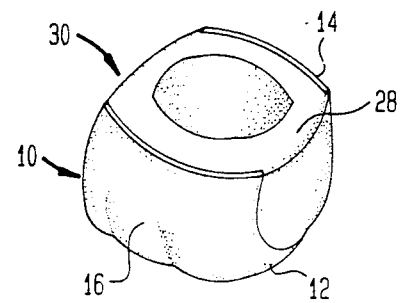
FIG. 11 is a bottom perspective view of the temporary crown of FIG. 10.
Figure 12:
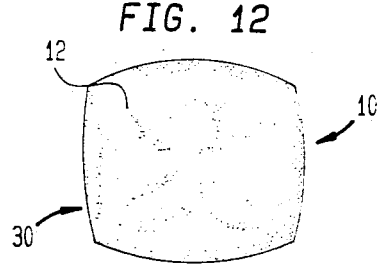
FIG. 12 is a top plan view of the temporary crown of FIG. 10.
Figure 13:
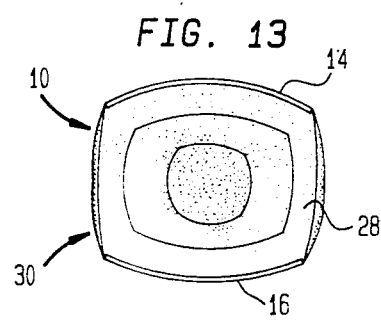
FIG. 13 is a bottom plan view of the temporary crown of FIG. 10.
Figure 14:
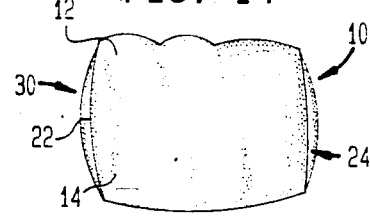
FIG. 14 is a buccal side plan view of the temporary crown of FIG. 10.
Figure 15:
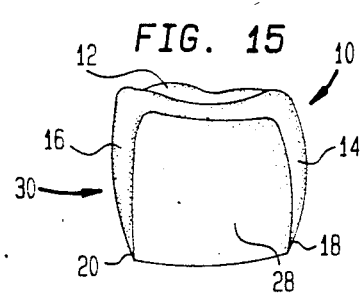
FIG. 15 is a mesial end plan view of the temporary crown of FIG. 10.

In using shell 10 according to the present invention, a tooth 26 which is to have the crown formed thereon, is prepared to receive a crown by grinding the tooth to the proper contour, as shown in FIG. 8. Then, after selecting the proper widths (that is, between adjacent live teeth 25 and 27) of buccal and lingual sides 14 and 16, shell 10 is adjusted by cutting or other suitable means to fit the contour of the gum line about the prepared tooth 26. Shell 10 is then filled with a self-curing acrylic resin in an unhardened state, as shown in FIG. 7, and positioned over the prepared tooth 26, as shown in FIG. 9, such that buccal and lingual sides 14 and 16 of shell 10 cover the buccal and lingual sides of prepared tooth 26, and free edges 18 and 20 of buccal and lingual sides 14 and 16, respectively, are proximate to the adjacent gingival surface about the prepared tooth 26. The patient is then guided to full closure of his mouth in the most repeatable bite position and the acrylic resin begins to set. When shell 10 is initially positioned over the prepared tooth 26, the acrylic resin oozes out from the mesial and distal sides, as shown in FIG. 9. This excess acrylic resin can be trimmed to provide for precise interproximal contact areas. During the setting operation, the self-curing acrylic resin bonds to prefabicated shell 10 to form the temporary dental crown.

Figure 16:
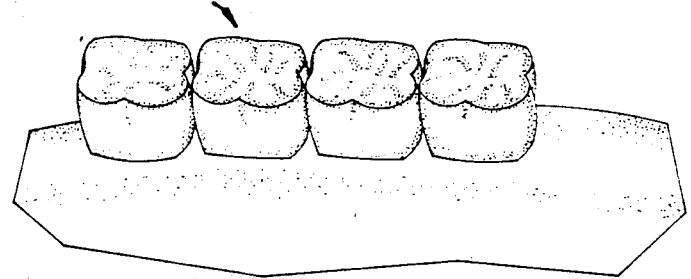
FIG. 16 is a perspective view of the temporary crown of FIG. 10 cemented in position on the ground down tooth prepared for receiving the temporary crown.

Prior to acrylic resin 28 reaching its final hardness, temporary shell 10 with acrylic resin 28 bonded thereto is snapped off the prepared tooth 26. At this time, after acrylic resin 28 has reached its final hardness, the now formed temporary dental crown 30, as shown in FIGS. 10-15, is shaped and polished outside of the mouth. Temporary dental crown 30 is then checked in the mouth for fit, and then cemented on prepared tooth 26 with a temporary cement (not shown), as shown in FIG. 16.

Thus, with the present invention, an improved temporary dental crown is produced which more accurately conforms to the patient's mouth, due in part to the open mesial and distal sides 22 and 24 of shell 10. As a result, a temporary crown having superior contour, and occlusal and proximal contact is provided. In addition, because mesial and distal sides 22 and 24 are open, shell 10 is much easier and less expensive to manufacture and use then conventional shells.

Having described a specific preferred embodiment of the invention with reference to the accompanying drawings, it will be appreciated that the present invention is not limited to that precise embodiment, and that various changes and modifications may be effected therein by one of ordinary skill in the art without departing from the scope or spirit of the invention as defined in the appended claims.

What is claimed is:

1. A temporary dental prothesis made of plastic material to be fitted on a prepared tooth to receive a permanent crown comprising:
   a. shell means of a generally fixed dimensional shape having a transverse wall means defining an occlusal layer configuration on the outer surface thereof, said transverse wall means having a buccal side and a lingual side,
   b. first sidewall means connected at one end to said buccal side of said transverse wall means and defining a buccal layer configuration on the outer surface thereof,
   c. said first sidewall means having a first shaped free edge remote from the end of the first sidewall means connected to the buccal side of the transverse wall means disposed in assembled position proximate to the gingival surface about said prepared tooth, and said first sidewall means reducing in thickness from said point of connection to the buccal side of said transverse wall means to said free edge on said first sidewall means,
   d. second sidewall means connected at one end to said lingual side of the transverse wall means and defining a lingual layer configuration on the outer surface thereof,
   e. said second sidewall means having a second shaped free edge remote from the end of the second sidewall means connected to said lingual side of the transverse wall means disposed in assembled position proximate to the gingival surface about said prepared tooth, and said second sidewall means reducing in thickness from said point of connection to the lingual side of said transverse wall means to said free edge on the second sidewall means,
   f. said shell means having fully formed openings at the mesial and distal ends thereof, and
   g. said transverse wall means, first sidewall means, and second sidewall means forming a cavity in the shell means fully open at the mesial end and the distal end of the shell means for receiving a self-curing acrylic resin.

2. The method of making a temporary dental prothesis for a tooth prepared to receive a Permanent Crown the steps of:

a. grinding and shaping a tooth to form a prepared tooth for receiving the permanent crown thereon, b. forming a shell means from plastic material which has a buccal side wall with a first free edge, a lingual side wall with a second free edge, and fully formed openings on the mesial and distal end thereof so as to define a cavity therein in communication within the said fully formed openings at the mesial end and distal end of the shell means, c. filling the cavity in said shell means with a self-curing acrylic resin material in the unhardened state, d. positioning and pressing said filled shell means over the prepared tooth until the respective first and second free edges of the buccal and lingual side of said shell means are proximate to the adjacent gingival surface about the prepared tooth and a sufficient amount of the unhardened acrylic resin escapes from the cavity through the openings at the mesial end and distal end of the shell means;

e. permitting the acrylic resin in the shell means in assembled position on the prepared tooth to partially harden and to bond to said shell means to form a preset temporary dental prothesis, f. shaping the temporary dental prothesis in situ and removing the same before the acrylic resin hardens and sets, and g. finishing the shaping and polishing of the said preset temporary dental prothesis after it is removed from the prepared tooth.

3. The method according to claim 2 wherein the pressing of the shell means onto the prepared tooth to form the preset temporary dental prothesis includes, the step of, having the patient exert a biting force on the shell means after it is positioned on the prepared tooth.

4. The method according to claim 2 including, the further step of removably cementing said finished temporary dental prothesis into assembled position on said prepared tooth.

* * * * *